United States Patent [19]

Simpson et al.

[11] 4,293,307

[45] Oct. 6, 1981

[54] METHOD AND APPARATUS FOR ANALYZING LIQUID

[75] Inventors: Roger J. Simpson, Sevenoaks; Janet A. Gawthorpe, Orpington; C. Alexander Lawrence, London, all of England

[73] Assignee: Saint Peter's Research Trust Limited, England

[21] Appl. No.: 20,777

[22] Filed: Mar. 15, 1979

[30] Foreign Application Priority Data

Apr. 5, 1978 [GB] United Kingdom ............... 13293/78

[51] Int. Cl.³ .................... G01N 27/40; G01N 33/48
[52] U.S. Cl. ............................. 23/230 B; 204/195 P; 422/81
[58] Field of Search ............... 422/82, 81, 68, 101; 210/500 M; 204/195 P, 195 M; 23/230 B

[56] References Cited

U.S. PATENT DOCUMENTS

| 3,572,994 | 3/1971 | Hochstrasser | 422/82 |
| 3,615,234 | 10/1971 | Ludvigsen | 422/82 |
| 3,658,478 | 4/1972 | Spergel et al. | 422/81 |
| 3,698,870 | 10/1972 | De Jong | 422/82 |
| 3,874,850 | 4/1975 | Sorensen et al. | 422/81 |
| 4,172,770 | 10/1979 | Semersky et al. | 204/195 P |

*Primary Examiner*—Ronald Serwin
*Attorney, Agent, or Firm*—William A. Drucker

[57] ABSTRACT

Method and apparatus for analyzing a liquid such as blood, and in particular analyzing certain constituents such as potassium or calcium ions, or dissolved gases comprising withdrawing the constituents from the liquid into a carrier fluid, which may or may not be derived from the liquid itself and analyzing the carrier fluid. In this way, for example, the analysis apparatus is not contaminated by undesired constituents, such as protein molecules of the liquid under test.

14 Claims, 1 Drawing Figure

U.S. Patent
Oct. 6, 1981
4,293,307
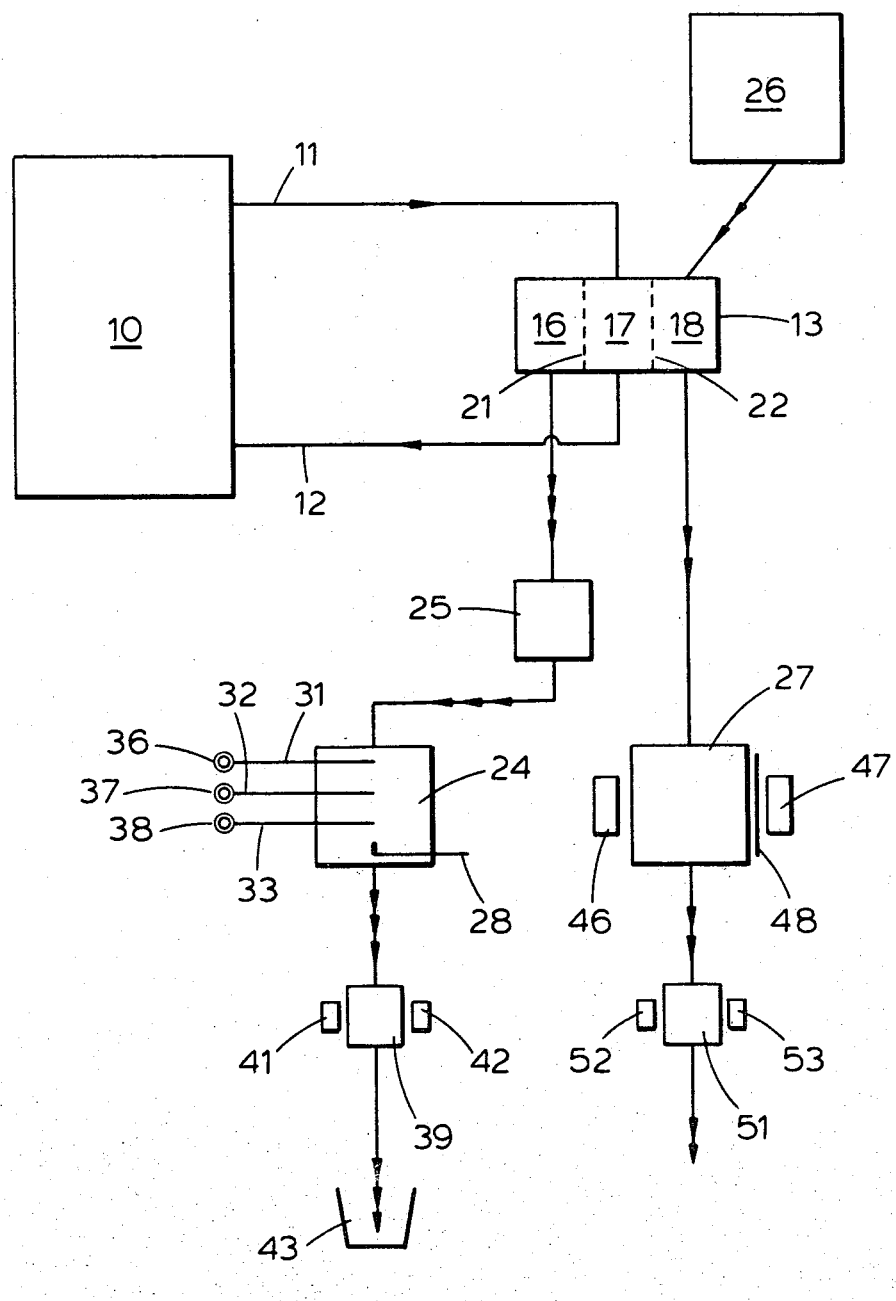

METHOD AND APPARATUS FOR ANALYZING LIQUID

The present invention relates to apparatus and method for analysing a liquid and in particular for determining the presence or absence of particular constituents in, for example, blood.

There are generally two ways of analysing a liquid for its various constituents. The first of these is a non-continuous sampling method in which a volume of the liquid is taken and is then analysed for the various constituents under consideration.

The second method is a continuous analysis method in which all or part of the liquid is allowed to pass through an analytical apparatus.

An advantage of the first method is its accuracy but two serious disadvantages are the time taken for the test and the quantity of the liquid that must be removed and cannot thereafter be replaced in the bulk of the liquid. An advantage of the second method is that the liquid which is used for sampling is flowing continuously and therefore takes into account variations in the constituents as they occur. Also the liquid after analysis is usually returned to the bulk of the liquid. However, a problem is that the analytical apparatus contacts the liquid and, particularly if the liquid is blood there is a risk of contamination of ion-selective electrodes in the apparatus by the blood.

There is therefore a desire for the continuous analysis of a liquid such as blood which is safe and will not contaminate the analysing means so that the variations in the levels of the various constituents of the blood may be continuously recorded and the blood after analysis may be returned to the patient's body. There is a similar desire for a similar analytical technique for other liquids as will be readily clear.

The invention provides according to one aspect, a method and apparatus for continuously analysing a flow of blood from a patient which may thereafter be returned to the patient.

According to a second aspect, the invention provides a method of analysing a flow of liquid such as blood comprising withdrawing at least part of the desired constituents to be analysed from the liquid and continuously analysing a carrier fluid containing the withdrawn constituents. According to a third aspect the invention provides apparatus for analysing a liquid such as blood including a passage for the liquid, means for withdrawing at least part of the desired constituents to be analysed from the liquid and means for analysing a carrier fluid containing the withdrawn constituents to determine the constituents.

In a first arrangement the carrier fluid may be a separate fluid (and in a preferred example to be described will be a gas) and in a second arrangement the carrier fluid may also be provided by the liquid (and in a preferred embodiment the carrier fluid is water separated from the blood under test).

An advantage of the second and third aspects of the invention is that part of the liquid or blood does not come into contact with the analysing means. There is therefore less risk of contamination of the analysing means.

The second and third aspects will give qualitative results. For example, it is easy to determine by using this method whether or not there are particular ions or gases present in the liquid. However, for quantitative results it is necessary to withdraw the desired constituents to be analysed from the liqud in such a way that their concentrations in the liquid and the carrier fluid substantially reach equilibrium or are in known proportion and means may be provided to carry this out.

Such a means may comprise a membrane, one side of the membrane being in contact with the liquid to be analysed and the other side of the membrane being in contact with the carrier fluid, the membrane being permeable to the constituents to be analysed.

Membranes are available which are permeable to gases, or alternatively to water and dissolved ions, in the former case, the carrier fluid may be an inert gas such as nitrogen and in the latter case, the carrier fluid may be the water passing through the membrane.

In either case, the analysis of the gas or dissolved ions in the carrier fluid may be carried out electrochemically by means of electrodes which are sensitive to the particular constituent in question and reference electrodes.

The apparatus may be calibrated by passing a control liquid in place of the liquid or blood through the apparatus having known proportions of constituents and noting the output readings, or alternatively by collecting the carrier fluid after analysis and carrying out standard analysis of this fluid.

A preferred arrangement of the invention will now be described by way of example only and with reference to the accompanying diagram of a blood analysis apparatus.

Although described here as a blood analyser the techniques are clearly applicable to the analysis of other liquids in, for example, fermentation processes, brewing or effluent treatments.

The apparatus to be described is for the direct analysis of a patient's blood to give the concentration of certain constituents of clinical importance. The apparatus consists of two related but separate systems one for the measurement of electrolytes such as potassium calcium, fluoride or other ions and the other for the estimation of the partial pressures of dissolved gases such as carbon dioxide, ammonia, oxygen and anaesthetic agents.

In practice, only one half need be used at any one time and the apparatus may be simplified for certain uses by only providing the electrolyte or the dissolved gas analysis.

The apparatus to be described is attached externally to the patient 10 and is connected to an artery and a vein. Flexible tubes 11,12 lead from the patient to the apparatus, blood passing from the patient 10 to the apparatus via tube 11 and from the apparatus back to the patient via tube 12.

The flexible tubes are preferably silicone rubber tubing or other non-toxic hypothrombogenic material.

A cell 13 is provided of any desired shape such as to make it most efficient and most easily cleaned, the cell 13 being divided into three compartments 16,17,18 which are shaped to avoid stagnent regions in which clots might form. Blood from the patient 10 passes through the tube 11 and through the central compartment 17. The compartments 16 and 17 are divided by a disc-like membrane 21 and compartments 17,18 are divided by disc-like membrane 22. The membrane 21 is of a type commercially available which allows for the passage only of electrolytes and water and the membrane 22 is of a type, also commercially available, which allows for the passage of dissolved gases only. The arrangement is such as to provide a relatively rapid flow past the surface of the ion/water permeable membrane to prevent a build-up of macromolecules with resultant reduction in filtration rate.

The gas porous membrane may be of thin silicone rubber or of microporous polypropylene (celgard 2500). The ion/water membrane may be ultrafiltration membranes made by Amicon or Millipore, or 'Cuprophan' which is used in artificial kidneys. The Amicon or Millipore ultrafiltration membranes have sharply defined molecular weight cut-off points above which they will not permit passage. Membranes with 10,000 and 30,000 MW cut-off are preferred.

The compartment 16 is connected to an electrolyte by fine flexible tubes analysis units 24. There is provided a peristaltic pump 25 between the compartment 16 and the electrolyte analysis unit 24 which can be used to regulate the flow of the liquid between the compartment 16 and the unit 24.

The compartment 18 is connected to a carrier gas supply 26 and the gas passing through the compartment 18 is passed to a dissolved gas analysis unit 27.

The electrolyte analysis unit 24 consists of a thermostatically controlled cell of small volume into which are inserted one or more ion selective electrodes 31,32,33 responding to ions such as potassium, calcium or sodium. Downstream from the electrodes is positioned the tip of a reference electrode 28. The potentials of the electrodes 31,32,33 are measured with respect to the reference electrode 28 using respective high input impedence millivoltmeters 36,37,38. The meters 36,37,38 are calibrated non-linearly in concentration. Alternatively the same high input impedance millivoltmeter would be used for each electrode in turn, readings of each parameter being taken every five minutes or so. Analogue or digital signal processing can be used to give a direct concentration reading.

On leaving the electrolyte analysis unit 24 the liquid passes through a small transparent chamber 39. A light sourse 41 and photodetector 42 on the opposite side are provided to check the transparency of the fluid. Alternatively, the chamber 39 may be provided before the unit 24.

Finally the liquid is allowed to fall in drops into a waste container 43. A light source (not shown) and photodetector may be provided with an electronic timer to give off a warning should the interval between drops of waste liquid become abnormal i.e. too long indicating membrane blockage or pump failure or too short indicating membrane rupture.

The dissolved gas analyser unit 27 comprises a cell having windows transparent to infra-red radiation in the required regions of the spectrum. There is a source 46 of radiation of a suitable wavelength preferably a black body with suitable filter and a photodetector 47, the photodetector 47 detecting through a suitable filter radiation of a wavelength which is strongly absorbed by the gas to be measured. By selection of the filter 48, with either the same photodetector 47 or different photodetectors, different gases may be analysed.

A similar arrangement for detecting membrane rupture is provided in the form of a small transparent chamber 51, a light source 52, and a photodetector 53 to check the transparency of the gas.

The presence of a suitable gas flow can be detected by a cooling effect on a hot wire forming part of an electrical bridge. The gas passes from the unit 27 to waste through tube 54.

The tubes connecting the various components of the apparatus are all fine bore so as to minimise the quantity of liquid or gas in the system.

In use, the tubes 11 and 12 are suitably connected to arteries and veins in the patient 10. The carrier gas supply 26 is connected to the cell 13 and the pump 25 switched on to provide a metered flow of water and ions through the membrane 21, through the compartment 16 to the unit 24. Similarly, gas is passed from the supply 26 through the compartment 18 to the unit 27 and although not shown some metering device may be provided corresponding to the pump 25. Blood thereby passes through the central compartment 17 and back to the patient. Water and ions pass through the membrane 21 and the concentration of the ions in the water reaches an equilibrium dependent on their concentration in the blood. In most circumstances, the concentrations would be identical but under certain circumstances, perhaps depending on flow rate and other variable factors, the concentrations may not be identical but will be of a predetermined proportion. Dissolved gas in the blood passes through the membrane 22 into the gas 26 until an equilibrium is set up between the concentration of the dissolved gas in the blood and the concentration of that dissolved gas in the carrier gas.

After passing through the central compartment 17 the blood returns to the patient, the net effect having been that some of the ions, water and dissolved gas in the blood has been removed but since the quantities involved are small this has no noticeable effect on the patient's blood system. Furthermore, the blood only comes into contact with tubes 11 and 12 and the inside of the compartment 17 and the membranes 21 and 22 all of which are non-toxic hypothrombogenic materials and are easy to maintain clean and sterile. Some components may be disposable.

The liquid from the compartment 16 is controlled to pass at a predetermined rate by the pump 25 (e.g. 50–350 μl/min) which under some circumstances may be drawing fluid from the cell 16 and in other circumstances may be slowing down the flow. The liquid passes to the analysis unit 24. After equilibrium has been obtained the meters 36, 37, 38 indicate the concentrations of the various electrolytes. The liquid passes from the unit 24 to the chamber 39. In the event of the membrane 21 rupturing, blood would pass into the carrier liquid and would colour the liquid passing through the transparent chamber 39 so that the light would be cut off from the detector 42. The peristaltic pump 25 would then automatically be switched off effectively cutting off the flow and a warning given.

After leaving chamber 39, the liquid passes away as described.

The carrier gas from the compartment 18 continuously passes to the analysis unit 27. After equilibrium is obtained so that the relative partial pressures of the gas in the blood and in the carrier gas are known, the analyser unit 27 is operated. Carbon dioxide absorbs light of a specific wavelength and thus by measuring the amount of light of that wavelength by means of the cell 47 the amount of carbon dioxide in the carrier gas can be readily measured. In a simpler apparatus $CO_2$ may be measured using an electrode.

The concentration of oxygen in the carrier gas can be measured by a conventional analyser or other means.

As before the presence of blood in the gas stream which would indicate that the membrane 22 would have ruptured could be checked by the chamber 51.

The apparatus can be used to simply provide a qualitative analysis of the blood. For example, it can be utilised to measure whether or not there are ions or gas of a predetermined type present in the blood. Alternatively, it is often necessary to know in a clinical situation when the concentration of a particular ion or gas increases or decreases and the apparatus can then simply be set up and variations in the level of the particular gas or ion under consideration noted.

If however it is required to provide a quantitative measure of the ion and concentration of gas and dissolved gas concentration in the blood, then there are several ways of calibrating the apparatus. In the first of these, before or after the analysis, in place of the blood being provided, a predetermined known blood sample may be passed through the compartment 17 with a known level of ion concentration and gas concentrations and the readings of the various meters noted.

A second way of calibrating apparatus is to collect the waste gas and waste liquid and to analyse them on a batch basis according to a conventional method. These may then provide an indication of the levels of the dissolved gas and ions in the blood and their relationship to the indications on the various meters. Thirdly, one may analyse effluent liquid leaving electrode cell, or take independent blood samples from the patient for check analysis.

The present apparatus can therefore be utilised to provide a continuous monitoring of the concentrations of various components of the blood of a patient without allowing that blood to come into contact with complex analysing means such as the various electrodes. It has particular use in the above described mode of operation where it is required in the clinical situation to know when the particular level of a constituent of the blood varies and can provide an immediate indication of this variation whereas hitherto this has not been possible.

Furthermore, the apparatus can be used with tubing already connected to the patient for the purpose of dialysis, or with canuli inserted in blood vessels. It may be done at the time of dialysis, or when the patient is not connected to the dialyser.

The invention is not restricted to the details of the foregoing example. For example, the cell 13 may be simplified to simply provide a membrane which either passes gas or passes the ions as desired in which case it will only be necessary to have two compartments and one membrane. Alternatively, two separate cells 13 may be provided, one for separating the blood and gas and one for separating the blood and ions.

If necessary the separation of dissolved gases or of water and ions could be effected using several similar cells in series or parallel to obtain an increased membrane area without making the overall dimensions of the unit too great.

Furthermore, other methods of analysing the carrier liquid or the carrier gas may be utilised as are well known. Other means for controlling the flow of the carrier liquid may be provided other than the peristaltic pump 25.

What we claim is:

1. Apparatus for continuously analyzing a continuous flow of liquid blood comprising
    separation means for continuously separating from the blood at least part of the ions to be analyzed, said separation means including
        a cell divided by a semi-permeable membrane into first and second compartments, the first compartment being connected to blood supply means to continuously receive blood therefrom and to means for continuous blood delivery, the semi-permeable membrane being of a type to allow the ions to be analyzed to pass continuously together with some water from the first compartment to the second compartment an analyzer having at least one ion selective electrode and reference electrode, means for passing the water and ions continuously from the second compartment to said analyzer means, and means for measuring the potentials of the electrodes for determining the concentrations of the ions.

2. Apparatus, as claimed in claim 1, in which said means for supplying blood comprises a tube of non-toxic hypothrombogenic material.

3. Apparatus, as claimed in claim 1 or claim 2, in which said means for delivery of blood comprises a tube of non-toxic hypothrombogenic material.

4. Apparatus, as claimed in claim 1, in which said means to pass the water and ions to the analyzer means comprises a tube.

5. Apparatus, as claimed in claim 1, in which said semi-permeable membrane has a sharply defined molecular weight cut off point of 10,000 to 30,000 MW above which it will not permit passage of molecules.

6. Apparatus for continuously analyzing ions in a continuous flow of liquid blood comprising
    separation means for continuously separating from the blood at least part of the ions to be analyzed, said separation means including
        a cell divided by a semi-permeable membrane into first and second compartments, the first compartment being connected to blood supply means to receive blood continuously therefrom and to means for continuous blood delivery, the semi-permeable membrane being of a type to allow the ions to be analyzed to pass continuously from the first compartment to the second compartment and having a sharply defined molecular weight cut off point between 10,000 to 30,000 MW above which it will not permit passage of ions and molecules,
    an analyzer means having at least one ion selective electrode and reference electrode, means for passing ions continuously from the second compartment to said analyzer means, and means for measuring the potentials of the electrodes for determining the concentrations of the ions.

7. Apparatus, as claimed in claim 6, including means for indicating blockage or rupture of the semi-permeable membrane.

8. Apparatus, as claimed in claim 7, in which said means to indicate membrane blockage or rupture comprises means to allow the water and ions after analysis to fall in drops, and means for detecting the interval between the drops.

9. Apparatus, for continuously analyzing blood comprising
    means for continuously supplying blood,
    means for delivery of the blood,
    separation means connected to the withdrawing means for separating from the blood at least part of the constituents which are to be analyzed, said separating means including
        a cell divided by two-semi-permeable membranes into first, second and third compartments, said first compartment being provided between the second and third compartments and being connected to said means for supplying blood to continuously receive blood therefrom and to the means for delivery of blood, the semi-permeable membrane between the first and second compartments being such as to allow ions to be analyzed to pass together with some water to the second compartment.

an analyzer means having at least one ion selective electrode and reference electrode, means to pass the water and ions to said analyzer means, means for measuring the potentials of the electrodes for determining the concentrations of the ions, said semi-permeable membrane between the first and third compartments being such as to allow dissolved gases to pass into the third compartment, a carrier gas supply connected to the third compartment, a gas analyzer unit connected to the third compartment and comprising a cell having windows transparent to radiation of the required wavelength, means for passing radiation of that wavelength through the gas and through the windows, and means for analyzing the transmitted radition to determine the gases and concentrations present.

10. Apparatus, as claimed in claim 9, including means, for detecting a rupture of the semi-permeable membrane between the first and third compartments, comprising a transparent chamber, a radiation source, and a photodetector to check the transparency of the gas.

11. Apparatus, as claimed in claim 9 or claim 10, in which the carrier gas supply means includes means to provide a metered supply of carrier gas to the third compartment.

12. A method for continuously analyzing blood comprising, continuously supplying blood,
continuously separating from the blood by means of a semi-permeable membrane at least part of the ions to be analyzed with some water,
continuously analyzing the water and ions by means of at least one ion selective electrode and reference electrode and continuously measuring the potentials of the electrodes for determining the concentrations of the ions.

13. A method, as claimed in claim 12, in which the water and ions are passed to the analyzing means by means of a peristaltic pump.

14. A method for continuously analyzing blood comprising
supplying blood,
continuously separating from the blood at least part of the ions to be analyzed with some water,
continuously analyzing the water and ions by means of at least one ion selective electrode and reference electrode, and
continuously measuring the potentials of the electrodes for determining the concentrations of the ions, continuously separating at least part of the dissolved gases from the blood, and
continuously analyzing said separated dissolved gases by passing radiation through the gases and analyzing the transmitted radiation to determine the gases and concentrations present.

* * * * *

UNITED STATES PATENT AND TRADEMARK OFFICE
CERTIFICATE OF CORRECTION

PATENT NO. : 4,293,307
DATED : October 6, 1981
INVENTOR(S) : R. J. Simpson et al.

It is certified that error appears in the above-identified patent and that said Letters Patent are hereby corrected as shown below:

Title page:

(73) Assignee: St. Peter's Research Trust Limited
and
Sira Institute Limited

Signed and Sealed this

Twenty-sixth Day of January, 1988

Attest:

DONALD J. QUIGG

Attesting Officer   Commissioner of Patents and Trademarks